United States Patent [19]

Honda et al.

[11] Patent Number: 4,866,176
[45] Date of Patent: Sep. 12, 1989

[54] 8-PIPERAZINYL-1,7-NAPHTHYRIDINE DERIVATIVE HAVING PHARMACEUTICAL ACTIVITY

[75] Inventors: Haruyoshi Honda, Tomisato; Yuko Yoshida, Chiba; Tadayuki Kouda, Narita; Hideaki Matsuda, Abiko; Tatsuhiko Katori, Tone, all of Japan

[73] Assignee: SS Pharmaceutical Co., Ltd., Tokyo, Japan

[21] Appl. No.: 84,836

[22] Filed: Aug. 13, 1987

[30] Foreign Application Priority Data

Aug. 19, 1986 [JP] Japan .................. 61-193095

[51] Int. Cl.$^4$ .................. C07D 471/06; C07D 401/14; A61K 31/475
[52] U.S. Cl. .................. 544/262; 514/254
[58] Field of Search .................. 544/362; 546/122; 514/254

[56] References Cited

U.S. PATENT DOCUMENTS

| | | | |
|---|---|---|---|
| 3,429,887 | 2/1969 | Lesher | 546/122 |
| 3,928,367 | 12/1975 | Mayer et al. | 546/122 |
| 4,168,311 | 9/1979 | Studeneer et al. | 546/90 |
| 4,176,183 | 11/1979 | Baldwin et al. | 546/123 |
| 4,659,710 | 4/1987 | Sato et al. | 544/362 |
| 4,690,924 | 9/1987 | Sato et al. | 546/122 |
| 4,716,170 | 12/1987 | Lesher et al. | 546/122 |

FOREIGN PATENT DOCUMENTS

| | | | |
|---|---|---|---|
| 208621 | 1/1987 | European Pat. Off. | 546/122 |
| 259882 | 7/1987 | France | 546/122 |

OTHER PUBLICATIONS

"The Japanese Journal of Pharmacology", published by The Japanese Pharmacological Society; Mar. 29–Apr. 1, 1987; vol. 43, Summary of Discussions.

"A New Synthesis of 1,7-Naphthyridine", by Rosita Tan et al., Tetrahedron Letters, No. 12, pp. 1233–1237, Pergamon Press Ltd.

Studeneer et al., CA83-114227 y (1975) "N,N-Dialkylamino-Carbamic Acid Esters of Substituted Hydroxypyridine Derivatives".

Baldwin et al., CA 90-54931 f (1979) Naphthyridines.

*Primary Examiner*—Cecilia Shen
*Attorney, Agent, or Firm*—Oblon, Spivak, McClelland, Maier & Neustadt

[57] ABSTRACT

A 8-piperazinyl-1,7-naphthyridine derivative represented by the following formula (I):

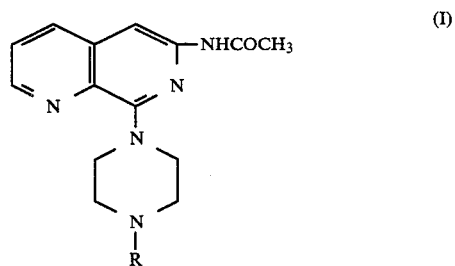

in which R represents a hydrogen atom, formyl group, acyl group, aroyl group, heteroaroyl group, substituted phenyl group, pyridyl group, aralkyl group or substituted or unsubstituted benzenesulfonyl group; and an acid adduct salt thereof. The compound has excellent antiinflammatory, antiarrhythmic and cardiotonic effects, and thus is useful as an antiinflammatory drug and a medicine for circulatory organs.

1 Claim, No Drawings

8-PIPERAZINYL-1,7-NAPHTHYRIDINE DERIVATIVE HAVING PHARMACEUTICAL ACTIVITY

BACKGROUND OF THE INVENTION

1. Field of the Invention:

This invention relates to a novel 8-piperazinyl-1,7-naphthyridine derivative and more particularly, to a 8-piperazinyl-1,7-naphthyridine derivative useful as a medicine.

2. Description of the Background:

A number of 1,7-naphthyridine derivatives are known in the art. Among them, those having a medicinal effects are the one having an antihypertensive effect (U.S. Pat. No. 4,176,183) and the one having an insecticidal effect (Federal Republic of Germany Patent Application Laid-open No. 2,361,438). There is no other 1,7-naphthyridine derivative reported in the art which has any medicinal effect.

In these circumstances, the inventors had synthesized various 1,7-naphthyridine derivatives and detected their medicinal effects, and found that specific 1,7-naphthyridine derivatives have an excellent medicinal effect. A patent was applied based on such a finding (Japanese Patent Application No. 67,875/1986).

SUMMARY OF THE INVENTION

The inventors have continued their efforts in synthesizing other various 1,7-naphthyridine derivatives and detecting their medicinal effects, and found that 8-piperazinyl-1,7-naphthyridine derivatives represented by the following formula (I):

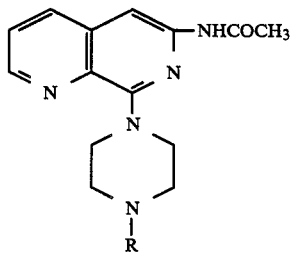

in which R represents a hydrogen atom, formyl group, acyl group, aroyl group, heteroaroyl group, substituted phenyl group, pyridyl group, aralkyl group or substituted or unsubstituted benzenesulfonyl group, have strong antiarrhythmic, cardiotonic, antiinflammatory and analgesic effects, and thus are effective for coronary disease, arthritis, lumbago, toothache and the like. Such findings have led to the completion of this invention.

Accordingly, an object of this invention is to provide a 8-piperazinyl-1,7-naphthyridine derivative represented by the above formula (I) and an acid adduct salt thereof.

The above and other objects, features and advantages of this invention will become apparent from the following description and the appended claim.

DETAILED DESCRIPTION OF THE INVENTION AND PREFERRED EMBODIMENTS

The 8-piperazinyl-1,7-naphthyridine derivative (I) of this invention may be prepared, for example, according to the following processes.

Process 1

8-halogeno-1,7-naphthyridine derivative (II) is reacted with a piperazine derivative (III) to obtain the compound of this invention (I), according to the following reaction formula:

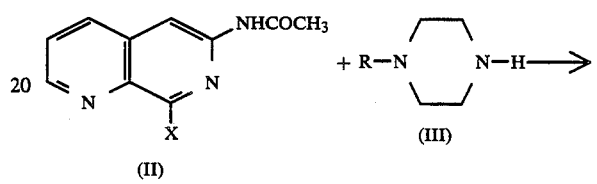

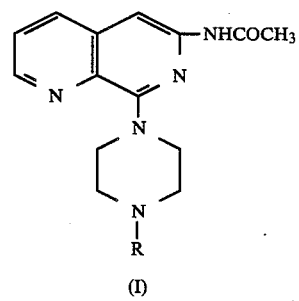

in which X represents a halogen atom and R has the same meaning as defined before.

The reaction can be carried out by agitating the reaction mixture with a solvent at room temperature to a reflux temperature of the solvent for several hours to several days. The solvent to be employed may be methanol, ethanol, aqueous alcohol, acetone, dimethylformamide, dioxane, ethoxyethanol and the like.

The reaction further may be carried out, as required, in the presence of a base such as sodium hydride, sodium hydroxide, potassium hydroxide and the like.

The starting material 8-halogeno-1,7-naphthyridine derivative (II) can be prepared according to methods known in the art, for instance, by reacting 6-amino-8-bromo-1,7-naphthyridine (IV) which can be prepared by the method proposed by Rosita Tan et al [Tetrahedron Letters, 1233–1237 (1966)] with acetic acid or a reactive derivative thereof in the presence of a base in accordance with the following reaction formula:

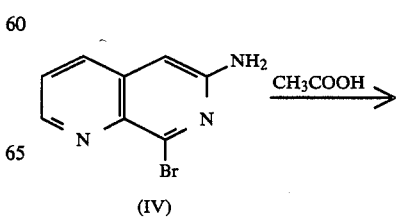

-continued

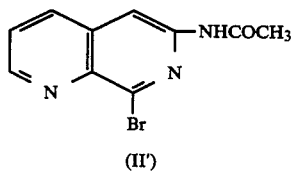

(II')

Process 2

The compound (Ia), which is a compound (I) in which the substituent in said formula (I) is a hydrogen atom, is reacted with a compound represented by the formula (V) in accordance with the following reaction scheme to obtain the compound (Ib).

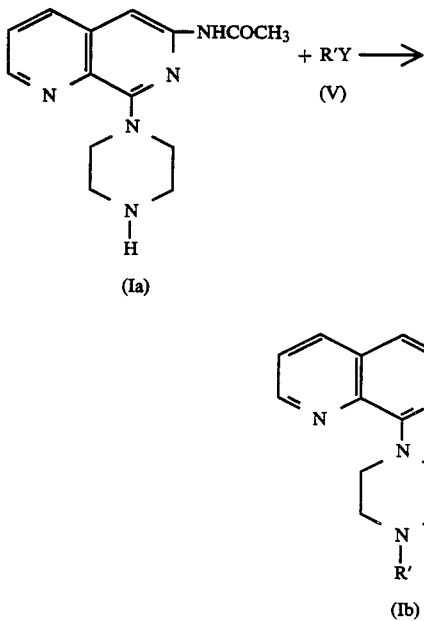

in which Y represents an eliminated group and R' represents formyl group, acyl group, aroyl group, heteroaroyl group, aralkyl group or substituted or unsubstituted benzenesulfonyl group.

The reaction can be carried out by agitating the reaction mixture with a solvent in the presence of a base at room temperature to a reflux temperature of the solvent for several hours to several days.

The base to be employed may be an organic base such as triethylamine, pyridine and the like, or an inorganic base such as sodium hydroxide, potassium hydroxide and the like. The solvent may be methylene chloride, chloroform, tetrahydrofuran, dioxane and The 8-piperazinyl-1,7-naphthyridine derivative (I) of this invention prepared as above may be converted, as required, into an inorganic salt such as hydrochloride, hydrobromide, sulfate and the like, or an organic salt such as maleate, fumarate, tartrate, citrate, methanesulfonate and the like.

Described below are the test results on medicinal effects of compounds of this invention prepared as illustrated in the above.

(1) Antiinflammatory effect

Wister rats (age 6 weeks), 5 of which consisted one group, were fasted for 18 hours and orally given a test compound which was dissolved or suspended in a 0.5% sodium carboxymethylcellulose (CMC-Na). Sixty (60) minutes after administration of the tested compound each rat was subcutaneously given 0.1 ml of 1% carragenin physiological saline at its right plantar, and 3 hours thereafter the volume of its foot (A) was measured. The rate of edematization was determined by the formula $[(A-B)/B] \times 100$, in which (A) is the thus-obtained volume of animals foot and (B) denotes the corresponding volume before administration of the compound (B).

The rate of edematization of controls which were subcutaneously given 0.1 ml of 1% carragenin physiological saline at their right plantars was also determined in the same manner. The rate of edema inhibition was determined on each of the tested compounds according to the following equation:

Edema Inhibition Rate =

$$\left(1 - \frac{\text{Rate of Edematization of Tested Animals}}{\text{Rate of Edematization of Controls}}\right) \times 100$$

The results are shown in Table 1, in which the compound numbers correspond those of Examples appearing hereinafter in this specification.

TABLE 1

| Compound No. | Dose (mg/kg) | Edema Inhibition Rate (%) |
|---|---|---|
| 1 | 30 | 64.8 |
| 2 | 30 | 35.0 |
| 8 | 30 | 28.6 |
| 9 | 30 | 30.4 |
| 22 | 30 | 57.1 |

As is apparent from the above results, the compound (I) of this invention possesses a strong antiinflammatory effect and thus is useful as antiinflammatory drug.

(2) Antiarrhythmic effect

Mice, age 5 weeks and weighing approximately 25 g, 6 of which consisted one group, were given a test compound which was dissolved in a 0.01 N–0.1 N hydrochloric acid solution (ip). Ten (10) minutes thereafter the mice were put into a sealed container which was filled with chloroform, their chests were incised promptly after confirming the respiratory arrest, and the heart rate was counted. Those with a 1–200 per minute heart rate were judged as positive in their antiarrhythmic effect. The results are shown in Table 2.

TABLE 2

| Compound No. | Dose (mg/kg) | Animals exhibited positive antiarrhythmic/Animals tested |
|---|---|---|
| 1 | 12.5 | 5/6 |
|  | 25.0 | 4/6 |
| 4 | 12.5 | 2/6 |
|  | 25.0 | 4/6 |
| 11 | 12.5 | 1/6 |
|  | 25.0 | 6/6 |
| 15 | 12.5 | 4/6 |
|  | 25.0 | 4/6 |
| 17 | 12.5 | 3/6 |
|  | 25.0 | 5/6 |
| Controls | — | 0/6 |

(3) Cardiotonic effect

Hearts of Hartley male guinea pigs, weighing 500–800 g, were taken out and their atrium muscles were enucleated in Krebs - hydrogencarbonate solution, to serve the same as samples for the test. The both ends of right and left atrium muscles with a spontaneous beat were fixed by means of Serres fines, and suspended, with their upper and lower portions being fixed, in a bath containing 20 ml of Krebs - hydrogencarbonate solution which was aerated by 95% $O_2$+5% $CO_2$ at 32° C. Then contractive forces of the spontaneous beat were isometrically measured. After the samples were stabilized, the test compound dissolved in 1 N hydrochloric acid solution and diluted by physiological saline to a concentration of $10^{-5}$ g/ml was charged into the bath. Maximum changes (%) of the contractive force after charging the test compound per the value obtained immediately before the charge were determined. The values obtained, which resprsent a positive inotropic effect, were made a standard for the cardiotonic effect.

The results are shown in Table 3.

TABLE 3

| Compound No. | Positive Inotropic Effect (% per the value obtained on controls) |
|---|---|
| 2 | 35.8 |
| 3 | 35.6 |
| 10 | 16.7 |
| 22 | 16.7 |

As illustrated above, the 8-piperazinyl-1,7-naphthyridine derivatives (I) of this invention have excellent antiinflammatory, antiarrhythmic and cardiotonic effects, and thus are useful as an antiinflammatory drug and a medicine for circulatory organs.

Other features of the invention will become apparent in the course of the following description of the exemplary embodiments which are given for illustration of the invention and are not intended to be limiting thereof.

EXAMPLES

Example 1

6-acetamido-8-(1-piperazinyl)-1,7-naphthyridine

To a mixture of 0.6 g of 6-acetamido-8-bromo-1,7-naphthyridine and 2.0 g of piperazine added was 25 ml of ethoxyethanol and the mixture was stirred for 1 hour under reflux. After reaction, ethoxyethanol was distilled off in vacuo, and the residue was added with chloroform, washed thoroughly with water and dried by anhydrous sodium sulfate. Chloroform was distilled off in vacuo, the residue obtained was purified by silica gel column chromatography. Then, 0.5 g of light yellowish crystal, 6-acetamido-8-(1-piperazinyl)-1,7-naphthyridine (Compound No. 1), was obtained by recrystallization from chloroform - ether mixed solvent (yield: 81.8%).

Example 2

6-acetamido-8-[4-(p-nitrobenzoyl)-1-piperazinyl]-1,7-naphthyridine

To a mixture of 0.24 g of 6-acetamido-8-(1-piperazinyl)-1,7-naphthyridine (Compound No. 1) and 0.1 g of triethylamine added was 15 ml of anhydrous methylene chloride, and the mixture was further added with 0.19 g of p-nitrobenzoyl chloride under ice-cooling, stirred for 3 hours at room temperature, washed with water and dried by anhydrous sodium sulfate. Methylene chloride was distilled off in vacuo, the residue obtained was purified by silica gel column chromatography. Then, 0.36 g of yellowish crystal, 6-acetamido-8-[4-(p-nitrobenzoyl)-1-piperazinyl]-1,7-naphthyridine (Compound No. 8), was obtained by recystallization from chloroform - ether mixed solvent (yield: 96.8%).

EXAMPLE 3

Compounds listed in Table 4 were prepared according procedures of Examples 1 or 2. Compounds as prepared by Examples 1 and 2 are also listed in Table 4.

Obviously, numerous modifications and variations of the present invention are possible in light of the above teachings. It is therefore to be understood that the scope of the appended claims, the invention may be practiced otherwise than as specifically described herein.

TABLE 4

| Com'd No. | —R | Characteristics NMR (δ) ppm | mp(° C.) |
|---|---|---|---|
| 1 | H | ($CDCl_3$)1.95(1H, s), 2.15(3H, s), 2.85~3.15(4H, m), 3.7~4.0(4H, m), 7.2(1H, dd), 7.65~8.0(3H, m), 8.4(1H, dd) | 186~189° |
| 2 | —CHO | ($CDCl_3$ + $CD_3OD$)2.2(3H, s), 2.8(1H, s), 3.4~4.1(8H, m), 7.3(1H, dd), 7.85(1H, s), 7.95(1H, dd), 8.05(1H, s), 8.6(1H, dd) | 237~239° |
| 3 | —$COCH_3$ | ($CDCl_3$)2.1(3H, s), 2.2(3H, s), 3.4~4.1(8H, m), 7.2(1H, dd), 7.6~8.0 (3H, m), 8.45(1H, dd) | 219~220° |
| 4 | 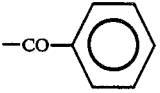 | ($CDCl_3$)2.15(3H, s), 3.5~4.1(8H, m), 7.1~7.4(6H, m), 7.7~8.0(3H, m), 8.4(1H, dd) | 205~206° |
| 5 | 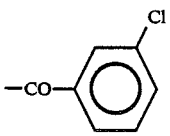 | ($CDCl_3$)2.15(3H, s), 3.5~4.1(8H, m), 7.1~7.3(5H, m), 7.7(1H, s), 7.7 ~8.0(2H, m), 8.4(1H, dd) | 172~174° |
| 6 | 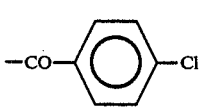 | ($CDCl_3$)2.15(3H, s), 3.5~4.2(8H, m), 7.1~7.4(5H, m), 7.7~7.9(3H, m), 8.45(1H, dd) | 214~216.5° |
| 7 | 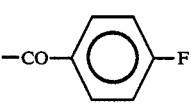 | ($CDCl_3$)2.2(3H, s), 3.6~4.2(8H, m), 6.9~7.6(5H, m), 7.8~8.1(3H, m), 8.6(1H, dd) | 226~229.5° |

TABLE 4-continued

| Com'd No. | —R | NMR (δ) ppm | mp(° C.) |
|---|---|---|---|
| 8 | —CO—C₆H₄—NO₂ (para) | (CDCl₃)2.2(3H, s), 3.7~4.15(8H, m), 7.2~8.1(6H, m), 8.25(2H, d), 8.6 (1H, dd) | 208~209.5° |
| 9 | —CO—C₆H₄—OCH₃ (para) | (CDCl₃)2.15(3H, s), 3.7(3H, s), 3.5~4.1(8H, m), 6.75(2H, d), 7.2(1H, dd), 7.25(2H, d), 7.7(1H, s), 7.7~7.95(2H, m), 8.45(1H, dd) | 202~204° |
| 10 | —CO—C₆H₃(OCH₃)₂ (3,4-dimethoxy) | (CDCl₃)2.2(3H, s), 3.7~4.2(14H, m), 6.8~7.5(4H, m), 7.8(1H, s), 7.95 (1H, dd), 8.6(1H, dd) | 209.5~211° |
| 11 | —CO—C₆H₂(OCH₃)₃ (3,4,5-trimethoxy) | (CDCl₃)2.15(3H, s), 3.5~4.1(17H, m), 6.5(2H, s), 7.2(1H, dd), 7.6~ 7.9(3H, m), 8.4(1H, dd) | 214~215° |
| 12 | —CO—(3-pyridyl) | (CDCl₃)2.2(3H, s), 3.6~4.2(8H, m), 7.2~7.5(2H, m), 7.6~8.2(4H, m), 8.5~8.8(3H, m) | 221~222.5° |
| 13 | —CO—(2-furyl) | (CDCl₃)2.25 (3H, s), 4.05(8H, s), 6.5(1H, dd), 7.05(1H, d), 7.25~7.6 (2H, m), 7.9~8.1 (3H, m), 8.65(1H, dd) | 176~177° |
| 14 | 2-Cl-C₆H₄— | (CDCl₃)21.5(3H, s), 3.05~3.4(4H, m), 3.95~4.2(4H, m), 6.8~7.35(5H, m), 7.5~7.9(3H, m), 8.45(1H, dd) | 199~200.5° |
| 15 | 3-Cl-C₆H₄— | (CDCl₃)2.15(3H, s), 3.2~3.5(4H, m), 3.95~4.2(4H, m), 6.5~7.35(5H, m), 7.5~7.9(3H, m), 8.5 (1H, dd) | 176~177° |
| 16 | 4-Cl-C₆H₄— | (CDCl₃)2.15(3H, s), 3.15~3.4(4H, m), 3.95~4.2(4H, m), 6.7(2H, d), 6.95~7.35(3H, m), 7.5~7.9(3H, m), 8.45(1H, dd) | 238~239° |
| 17 | 4-F-C₆H₄— | (CDCl₃)2.15(3H, s), 3.1~3.6(5H, m), 3.95~4.25(4H, m), 6.75(2H, s), 6.85(2H, s), 7.25(1H, dd), 7.7(1H, s), 7.85(1H, dd), 8.5(1H, dd) | 239~240° |
| 18 | 2-OCH₃-C₆H₄— | (CDCl₃)2.15(3H, s), 3.05~3.4(4H, m), 3.75(3H, s), 4.0~4.3(4H, m), 6.8(4H, br. s), 7.2(1H, dd), 7.65~7.9(3H, m), 8.45(1H, dd) | 194~195° |
| 19 | 4-OCH₃-C₆H₄— | (CDCl₃)2.15(3H, s), 3.05~3.3(4H, m), 3.65(3H, s), 3.9~4.2(4H, m), 6.7(4H, br. s), 7.2(1H, dd), 7.5~7.9(3H, m), 8.4(1H, dd) | 181~182° |

TABLE 4-continued

| Com'd No. | —R | NMR (δ) ppm | mp(° C.) |
|---|---|---|---|
| 20 | 3-methyl-(trifluoromethyl)phenyl | (CDCl$_3$ + CD$_3$OD)2.2(3H, s), 3.2~3.55(4H, m), 3.9~4.25(5H, m), 6.8~7.4 (5H, m), 7.7 (1H, s), 7.85 (1H, dd), 8.5 (1H, dd) | 186.5~187° |
| 21 | 6-methylpyridin-2-yl | (CDCl$_3$)2.15(3H, s), 3.5~3.8 (4H, m), 3.9~4.2(4H, m), 6.3~6.6 (2H, m), 7.05~7.4(2H, m), 7.6~7.9(3H, m), 8.0(1H, dd), 8.4(1H, dd) | 224~226.5° |
| 22 | —CH$_2$—phenyl | (CDCl$_3$)2.1(3H, s), 2.5~2.8(4H, m), 3.5(2H, s), 3.8~4.1(4H, m) 7.0~7.3 (6H, m), 7.5~7.9(3H, m), 8.4(1H, dd) | 169~170° |
| 23 | —CH(phenyl)$_2$ | (CDCl$_3$)2.10 (3H, s), 2.4~2.7(4H, m), 3.8~4.1 (4H, m), 4.15(1H, s), 6.9~7.4(11H, m), 7.5~7.9(3H, m), 8.35 (1H, dd) | 242~245° ( ) |
| 24 | —SO$_2$—(4-methylphenyl) | (CDCl$_3$)2.15(3H, s), 2.35(3H, s), 3.0~3.3(4H, m), 3.8~4.1(4H, m), 7.0~7.9 (8H, m), 8.35(1H, dd) | 218~219° |
| 25 | —SO$_2$—(4-chlorophenyl) | (CDCl$_3$)2.15(3H, s), 3.0~3.3(4H, m), 3.8~4.1(4H, m), 7.05~7.9 (8H, m), 8.4(1H, dd) | 224~226° |
| 26 | —SO$_2$—(4-fluorophenyl) | (CDCl$_3$)2.15 (3H, s), 3.0~3.3(4H, m), 3.8~4.1(4H, m), 6.85~7.3 (3H, m), 7.5~7.9(5H, m), 8.4(1H, dd) | 215~217.5° |

What is claimed as new and desired to be secured by Letters Patent of the United States is:

1. An 8-piperazinyl-1,7-naphthyridine derivative represented by the following formula (I):

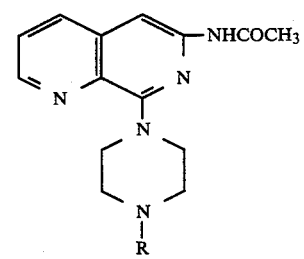

in which R represents a hydrogen atom; a formyl group; a lower alkanoyl group; a benzoyl group which may have one or more halogen atom, nitro group, or lower alkoxy group substituents; a furanylcarbonyl group; a pyridylcarbonyl group; a phenyl group which has one or more halogen atom, lower alkoxyl group, or trifluoromethyl group substituents; a pyridyl group; a benzyl group; a diphenylmethyl group, or a benzenesulfonyl group which may have one or more lower alkyl group or halogen atom substituents; or a pharmaceutically acceptable salt thereof.

* * * * *

UNITED STATES PATENT AND TRADEMARK OFFICE
CERTIFICATE OF CORRECTION

PATENT NO. : 4,866,176
DATED : Sep. 12, 1989
INVENTOR(S) : Susumu Sato, et al

It is certified that error appears in the above-identified patent and that said Letters Patent is hereby corrected as shown below:

On the title page

The names of the inventors are incorrectly recorded,
   "Haruyoshi Honda, Tomisato; Yuko Yoshida, Chiba;
   Tadayuki Kouda, Narita;   Hideaki Matsuda, Abiko;
   Tatsuhiko Katori, Tone, all of Japan" should be:

--Susumu Sato, Chiba; Haruyoshi Honda, Chiba;
   Teruo Koumoto, Chiba; Kazuo Isomae, Chiba;
   Tadayuki Kuraishi, Chiba; Tatsuhiko Katori, Ibaraki,
   all of Japan--

Signed and Sealed this

Tenth Day of April, 1990

*Attest:*

HARRY F. MANBECK, JR.

*Attesting Officer*   *Commissioner of Patents and Trademarks*